(12) United States Patent
Katta

(10) Patent No.: US 9,645,103 B2
(45) Date of Patent: May 9, 2017

(54) ANALYTE SENSOR AND ANALYTE SENSING METHOD

(71) Applicant: KYOCERA Corporation, Fushimi-ku, Kyoto-shi, Kyoto (JP)

(72) Inventor: Hiroshi Katta, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 364 days.

(21) Appl. No.: 14/375,780

(22) PCT Filed: Jan. 29, 2013

(86) PCT No.: PCT/JP2013/051887
§ 371 (c)(1),
(2) Date: Jul. 30, 2014

(87) PCT Pub. No.: WO2013/115175
PCT Pub. Date: Aug. 8, 2013

(65) Prior Publication Data
US 2015/0017735 A1 Jan. 15, 2015

(30) Foreign Application Priority Data

Jan. 30, 2012 (JP) ................................. 2012-016383
Mar. 28, 2012 (JP) ................................. 2012-074156

(51) Int. Cl.
*G01N 33/00* (2006.01)
*G01N 27/12* (2006.01)
(Continued)

(52) U.S. Cl.
CPC .............. *G01N 27/12* (2013.01); *G01N 5/02* (2013.01); *G01N 29/022* (2013.01); *G01N 29/30* (2013.01);
(Continued)

(58) Field of Classification Search
CPC ........... G01N 27/12; G01N 5/02; G01N 29/30
See application file for complete search history.

(56) References Cited

U.S. PATENT DOCUMENTS 5,478,756 A * 12/1995 Gizeli .................. G01N 29/022
310/311
7,170,213 B2 * 1/2007 Yamanaka ........... G01N 29/022
310/313 A
(Continued)

FOREIGN PATENT DOCUMENTS

JP 7-159381 A 6/1995
JP 2001-249118 A 9/2001
(Continued)

OTHER PUBLICATIONS

Hato et al, "Development of Novel SAW Liquid Sensing System with SAW Signal Generator" Technical Report of The Institute of Electronics, Information and Communication Engineers, Feb. 2003.
(Continued)

*Primary Examiner* — Sam P Siefke
(74) *Attorney, Agent, or Firm* — Procopio Cory Hargreaves and Savitch LLP

(57) ABSTRACT

A biosensor includes a detection element having an analyte detecting portion which is monotonically increased in mass in response to detection of an analyte; a reference element having a reference measuring portion which exhibits no reactivity to the analyte; a mixer which mixes a detection signal responsive to mass variations in the analyte detecting portion from the detection element and a reference signal from the reference element; a measurement which calculates two candidate phase-change values of a positive value and a negative value, from a signal mixed by the mixer in accordance with a heterodyne system, and determines a phase-change value from the two candidate phase change value by judging whether the phase is positive or negative based on temporal changes in signal strength; and a detection amount calculation portion which calculates a detection (Continued)

amount of the analyte based on the phase change value determined by the measurement portion.

9 Claims, 8 Drawing Sheets

(51) Int. Cl.
*G01N 5/02* (2006.01)
*G01N 29/02* (2006.01)
*G01N 29/30* (2006.01)

(52) U.S. Cl.
CPC ............... *G01N 2291/012* (2013.01); *G01N 2291/0256* (2013.01); *G01N 2291/0423* (2013.01)

(56) References Cited

U.S. PATENT DOCUMENTS

| | | | |
|---|---|---|---|
| 8,113,063 B2* | 2/2012 | Nakaso | G01N 29/022 73/861 |
| 2008/0085212 A1* | 4/2008 | Adams | G01N 29/036 422/50 |
| 2010/0170345 A1 | 7/2010 | Noguchi et al. | |
| 2013/0156644 A1* | 6/2013 | Lee | G01N 29/022 422/69 |
| 2015/0017735 A1 | 1/2015 | Katta | |
| 2016/0195498 A1* | 7/2016 | Katta | G01N 29/022 436/501 |

FOREIGN PATENT DOCUMENTS

| | | |
|---|---|---|
| JP | 2008-122105 A | 5/2008 |
| JP | 5421502 B1 | 2/2014 |
| WO | 2009-037977 A1 | 3/2009 |

OTHER PUBLICATIONS

International search report dated Mar. 12, 2013 issued in counterpart PCT application No. PCT/JP2013/051887.
Office Action dated Dec. 23, 2016 issued by the United States Patent Office in co-pending U.S. Appl. No. 14/894,885.

* cited by examiner (a)

(b)

(a)

(b)

(a)

(b)

ANALYTE SENSOR AND ANALYTE SENSING METHOD

TECHNICAL FIELD

The present invention relates to an analyte sensor capable of measuring properties of an analyte or a target substance contained in an analyte as well as to an analyte sensing method.

BACKGROUND ART

There is known a surface acoustic wave sensor for measuring properties or ingredients of an analyte liquid by means of a surface acoustic wave device.

The surface acoustic wave sensor, which is constructed of a piezoelectric substrate on which is mounted a detecting portion which reacts with a component contained in an analyte sample, is designed to detect the properties or ingredients of an analyte liquid by measuring electric signals responsive to variations in surface acoustic wave (SAW) propagating through the detecting portion (for example, refer to Patent Literature 1).

The SAW sensor disclosed in Patent Literature 1 measures the concentration of an analyte sample by detecting a phase difference in SAW. In order to make phase difference measurement, a quadrature modulation system has generally been adopted, because it offers an extended measurable phase range.

CITATION LIST

Patent Literature

Patent Literature 1: Japanese Unexamined Patent Publication JP-A 2008-122105

Non-Patent Literature

Non-Patent Literature 1: "Development of Novel SAW Liquid Sensing System with SAW Signal Generator" excerpted from the technical report of IEICE published in February, 2003 by The Institute of Electronics, Information and Communication Engineers

SUMMARY OF INVENTION

Technical Problem

However, the quadrature modulation system poses the following problems: the number of components constituting the system is large with a consequent difficulty in system downsizing; and the number of digital processing steps is large with a consequent increase in current consumption.

In light of this, there has been a demand for small-scale data processing method featuring lower current consumption and a biosensor equipped with the data processing method.

Solution to Problem

According to one aspect of the invention, an analyte sensor comprises: an analyte detecting portion; a detection element; a reference measuring portion; a reference element; a measurement portion; and a detection amount calculation portion. The analyte detecting portion is monotonically changed in mass in response to adsorption of a target provided in an analyte or reaction with the target. The detection element is configured to output a detection signal of AC responsive to mass variations in the analyte detecting portion. The reference measuring portion undergoes neither adsorption of a target nor reaction with the target. The reference element is configured to output a reference signal of AC relative to the detection signal. The measurement portion determines two candidate phase-change values of a positive candidate phase-change value and a negative candidate phase-change value, from a measurement signal which is obtained from the detection signal and the reference signal in accordance with a heterodyne system. At this time, case classification is carried out according to the following four conditions (1) to (4):

(1) where a mass of the analyte detecting portion is monotonically increased, and the detection signal is obtained by subtracting the reference signal from the detection signal in accordance with the heterodyne system;

(2) where the mass of the analyte detecting portion is monotonically decreased, and the detection signal is obtained by subtracting the detection signal from the reference signal in accordance with the heterodyne system;

(3) where the mass of the analyte detecting portion is monotonically increased, and the detection signal is obtained by subtracting the reference signal from the detection signal in accordance with the heterodyne system; and (4) where the mass of the analyte detecting portion is monotonically decreased, and the detection signal is obtained by subtracting the detection signal from the reference signal in accordance with the heterodyne system.

Under the condition (1) or (2), when measurement signal strength is decreased with time, the positive candidate phase-change value is outputted as a phase change value, and when measurement signal strength is increased with time, the negative candidate phase-change value is outputted as a phase change value.

Under the condition (3) or (4), when measurement signal strength is decreased with time, the negative candidate phase-change value is outputted as a phase change value, and when measurement signal strength is increased with time, the positive candidate phase-change value is outputted as a phase change value.

The detection amount calculation portion calculates the detection amount of the analyte on the basis of the phase change value.

According to one aspect of the invention, an analyte sensing method comprises: an analyte solution supplying step; a determination step; and a calculation step. In the analyte solution supplying step, an analyte solution containing an analyte in which a target is provided, is supplied to an analyte detecting portion of a detection element that is monotonically changed in mass in response to adsorption of the target or reaction with the target, and a reference detecting portion of a reference element that undergoes neither adsorption of the target nor reaction with the target. In the determination step, two candidate phase-change values of a positive candidate phase-change value and a negative candidate phase-change value, are determined from a measurement signal which is obtained from a detection signal of AC responsive to mass variations in the analyte detecting portion and a reference signal of AC relative to the detection signal from the reference detecting portion, in accordance with a heterodyne system. At this time, case classification is carried out according to the following four conditions (1) to (4):

(1) where a mass of the analyte detecting portion is monotonically increased, and the detection signal is obtained by subtracting the reference signal from the detection signal in accordance with the heterodyne system;

(2) where the mass of the analyte detecting portion is monotonically decreased, and the detection signal is obtained by subtracting the detection signal from the reference signal in accordance with the heterodyne system;

(3) where the mass of the analyte detecting portion is monotonically increased, and the detection signal is obtained by subtracting the reference signal from the detection signal in accordance with the heterodyne system; and (4) where the mass of the analyte detecting portion is monotonically decreased, and the detection signal is obtained by subtracting the detection signal from the reference signal in accordance with the heterodyne system.

Under the condition (1) or (2), when measurement signal strength is decreased with time, the positive candidate phase-change value is determined as a phase change value, and when measurement signal strength is increased with time, the negative candidate phase-change value is determined as a phase change value.

Likewise, under the condition (3) or (4), when measurement signal strength is decreased with time, the negative candidate phase-change value is determined as a phase change value, and, when the measurement signal strength is increased with time, the positive candidate phase-change value is determined as a phase change value.

In the calculation step, the amount of the analyte detected is calculated on the basis of the phase change value.

Advantageous Effects of Invention

According to the invention, it is possible to provide a compact analyte sensor featuring lower current consumption and an analyte sensing method.

DESCRIPTION OF EMBODIMENTS

Hereinafter, embodiments of an analyte sensor pursuant to the invention will be described in detail with reference to drawings. Note that, in each of the drawings as will hereafter be described, identical constituent members are identified with the same reference symbols. Moreover, the size of each member, the distance between the members, and so forth are schematically depicted and may therefore be different from the actual measurements.

Moreover, although any side of the analyte sensor may be either an upper side or a lower side, in the following description, for purposes of convenience, an x-y-z rectangular coordinate system is defined, and, words such as an upper surface, a lower surface, etc. are used on the understanding that a positive z direction is an upward direction.

(Principles of Analyte Sensor 100)

Figure 1:
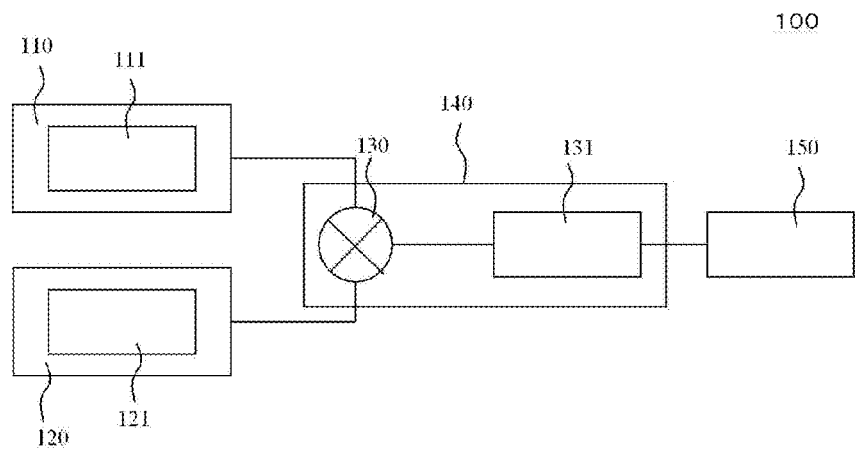
FIG. 1 is a principled configuration diagram showing an analyte sensor in accordance with an embodiment of the invention.

FIG. 1 is a schematic diagram for explaining the principle of an analyte sensor 100. As shown in FIG. 1, the analyte sensor 100 comprises a detection element 110; a reference element 120; a measurement portion 140; and a detection amount calculation portion 150.

In this embodiment, the detection element 110 includes an analyte detecting portion 111 which is monotonically increased in mass in response to adsorption of a target provided in an analyte or reaction with the target. For example, the analyte detecting portion 111 can be implemented by immobilizing a reactive group having such a reactivity as to undergo specific target adsorption on a Au film impervious to the influence of electrical characteristics such as electrical conductivity of an analyte. Note that there is no need for the analyte detecting portion to adsorb a target in itself. For example, a reactive group having such a characteristic as to react with a substance other than a target provided in an analyte resulting from reaction with the target may be immobilized on a Au film. It is preferable that this Au film is electrically short-circuited.

The reference element 120 includes a reference measuring portion 121. For example, the reference measuring portion 121 does not have such a reactivity as to specifically adsorb a target provided in an analyte or to cause substitution reaction with a substance contained in an analyte due to a conformational change. As a concrete example, a Au film free from immobilization of the aforementioned reactive group can be used.

A mixer 130 mixes a detection signal responsive to mass variations in the analyte detecting portion 111 from the detection element 110 and a reference signal from the reference element 120. In this case, the detection signal and the reference signal are AC signals, and, the reference signal serves as a fiducial signal in relation to the detection signal.

The measurement portion 140 performs two steps as set forth hereunder. At first, from a measurement signal mixed by the mixer 130, through a low-pass filter 131, a candidate phase-change value is calculated in accordance with a heterodyne system. The processing details of this step vary depending on the following four conditions. Concretely, case classification is carried out according to the following four conditions (1) to (4):

(1) where the mass of the analyte detecting portion 111 is monotonically increased, and the detection signal is obtained by subtracting the reference signal from the detection signal in accordance with the heterodyne system;

(2) where the mass of the analyte detecting portion 111 is monotonically decreased, and the detection signal is obtained by subtracting the detection signal from the reference signal in accordance with the heterodyne system;

(3) where the mass of the analyte detecting portion 111 is monotonically increased, and the detection signal is obtained by subtracting the reference signal from the detection signal in accordance with the heterodyne system; and (4) where the mass of the analyte detecting portion 111 is monotonically decreased, and the detection signal is obtained by subtracting the detection signal from the reference signal in accordance with the heterodyne system.

In the case where the mass of the analyte detecting portion 111 is monotonically increased, a detection signal falls behind in phase as compared to a reference signal. Therefore, when a detection signal is subtracted from a reference signal, there is a monotonic increase in phase change. On the other hand, when a reference signal is subtracted from a detection signal, there is a monotonic decrease in phase change.

Likewise, in the case where the mass of the analyte detecting portion 111 is monotonically decreased, a detection signal advances in phase as compared to a reference signal. Therefore, when a detection signal is subtracted from a reference signal, there is a monotonic decrease in phase change. On the other hand, when a reference signal is subtracted from a detection signal, there is a monotonic increase in phase change. This phenomenon is utilized.

Figure 10:
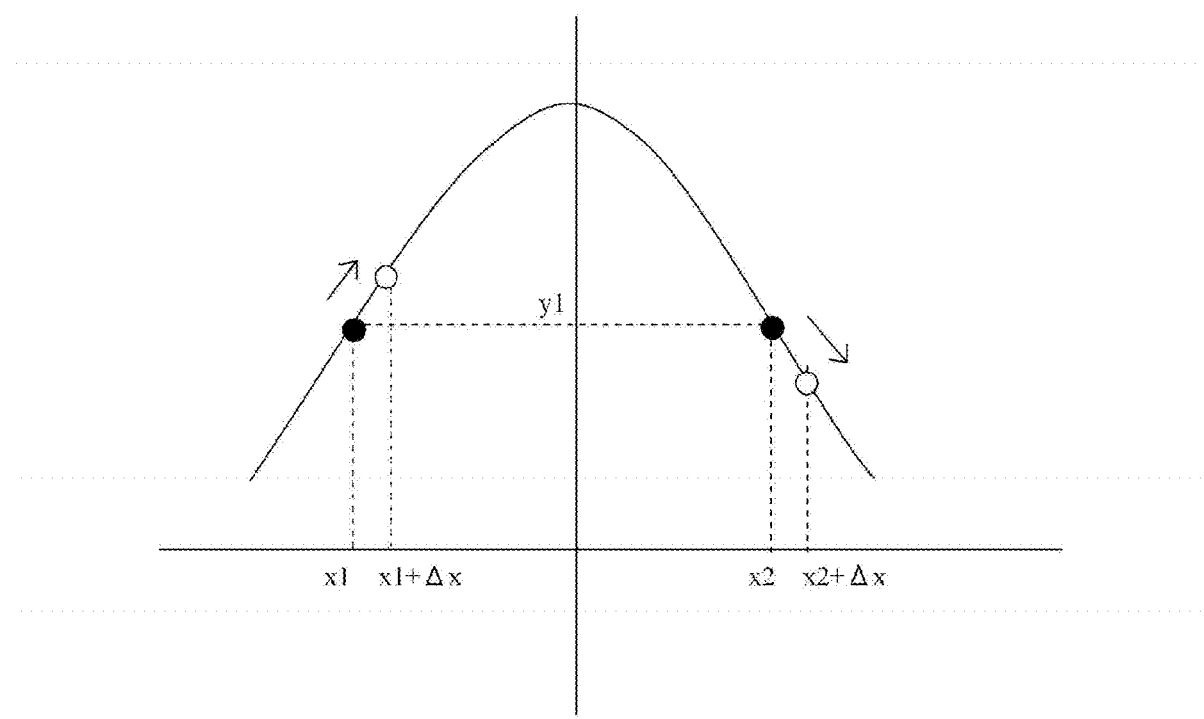
FIG. 10 is a graph showing a correlation between detection signal strength and phase in the analyte sensor shown in FIG. 1.

In giving a more concrete explanation, the condition (1) will be quoted by way of illustration. Since a measurement signal is processed by the heterodyne system, as shown in FIG. 10, the signal makes a sine curve which is positive-negative symmetrical about 0°, wherefore a candidate phase-change value corresponding to signal strength (output value) y1 takes on two negative and positive values, namely x1 and x2. Herein, FIG. 10 shows a locus curve indicative of a correlation between measurement signal strength and phase. Next, temporal changes in the signal mixed by the mixer 130 are confirmed. Since the analyte detecting portion 111 has the characteristic of being monotonically increased in mass, it follows that the phase of the measurement signal is monotonically increased with time. With the utilization of this characteristic, it will be found that, when the measurement signal strength is increased, the negative phase value x1 is assigned, and when the measurement signal strength is decreased, the positive phase value x2 is assigned. In other words, while signal strength varies with time ($\Delta x$), when the phase takes on the value x1, the strength of x1+$\Delta x$ is larger than y1. On the other hand, when the phase takes on the value x2, the strength of x2+$\Delta x$ is smaller than y1. Thus, a distinction can be made between x1 and x2 by determining whether the phase value becomes larger or smaller than the original strength (y1) with time. That is, whether the phase is positive or negative can be judged by examining temporal changes in the measurement signal mixed by the mixer 130. In this way, a decision is made between the two candidate phase-change values to determine a phase change value. Also in the case of the condition (2), a phase change value can be determined in a similar manner. By contrast, in the cases of the conditions (3) and (4), when the measurement signal strength is increased, the positive phase value is determined as the phase change value, and when the measurement signal strength is decreased, the negative phase value is determined as the phase change value.

Then, the detection amount calculation portion 150 calculates the detection amount of an analyte on the basis of the phase change value determined by the measurement portion 140.

By virtue of such a configuration, an analyte sensor 100 capable of calculating the detection amount of an analyte can be provided. In this construction, since signal processing operation is performed by the heterodyne system, it is possible to calculate the detection amount of an analyte only with the addition of the mixer 130 for deriving a differential between a detection signal and a reference signal. Accordingly, in contrast to the case of adopting the quadrature modulation system as has been conventionally used, the analyte sensor 100 does not necessitate complicated signal processing operation, has fewer necessary components, can be made lower in profile, and succeeds in reduction of current consumption. Moreover, in a normal heterodyne system, a judgment as to whether the phase is positive or negative cannot be made, wherefore measurable phases are limited to a range from 0° to 180°. However, according to the analyte sensor 100 of the present embodiment, by confirming temporal changes in signal, whether the phase is positive or negative can be judged from candidate phase-change values. This makes it possible to obtain a wider measurable phase range extending from −180° to 180°. Besides, by monitoring a signal continuously and examining the loci of the signal over time, it is possible to obtain an unlimited measurable phase range beyond the range from −180° to 180°.

In order to achieve such a widening of the measurable phase range, it is desirable to dispose the analyte detecting portion 111 which is monotonically increased in mass in response to analyte detection, as well as to carry out measurement signal sampling two or more times at time-spaced intervals. The measurement interval is determined in accordance with a rate at which a reaction to induce mass changes proceeds. It is more desirable to carry out measurement signal sampling consecutively.

As described hereinabove, it is possible to provide an analyte sensor 100 which is capable of detection with fewer constituent components and with fewer signal processing steps in a measurable phase range as wide as that of the quadrature modulation system.

(Structure of Analyte Sensor 100A)

Next, referring to FIG. 2, the structure of an analyte sensor 100A which is an embodiment of the principle of the analyte sensor 100 will be described.

Figure 2:
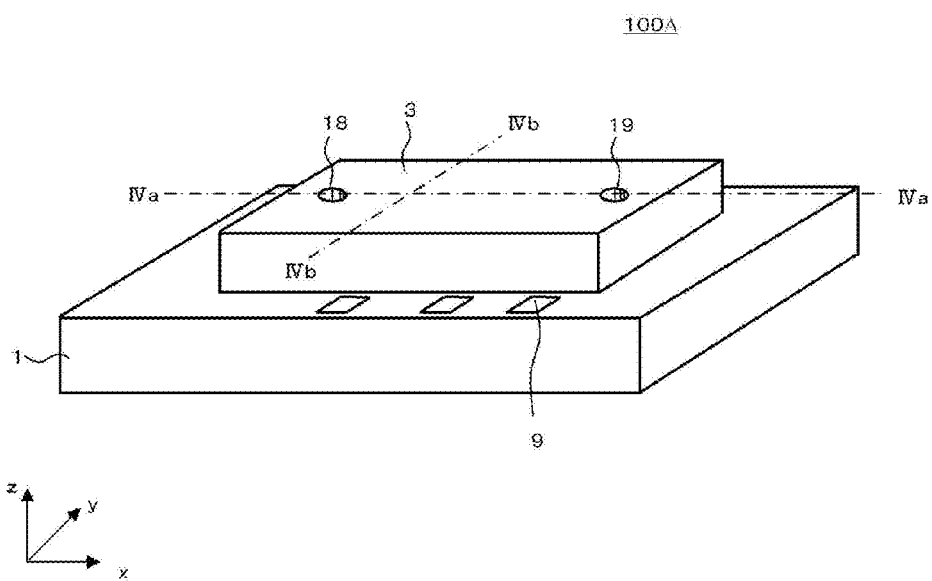
FIG. 2 is a perspective view of the analyte sensor in accordance with the embodiment of the invention.

As shown in FIG. 2 which is a perspective view, from the standpoint of appearance, the analyte sensor 100A is composed mainly of a piezoelectric substrate 1 and a cover 3. The cover 3 is formed with a first through hole 18 acting as an inlet for an analyte solution, and an air slot or a second through hole 19 acting as an outlet for an analyte solution.

Figure 3:
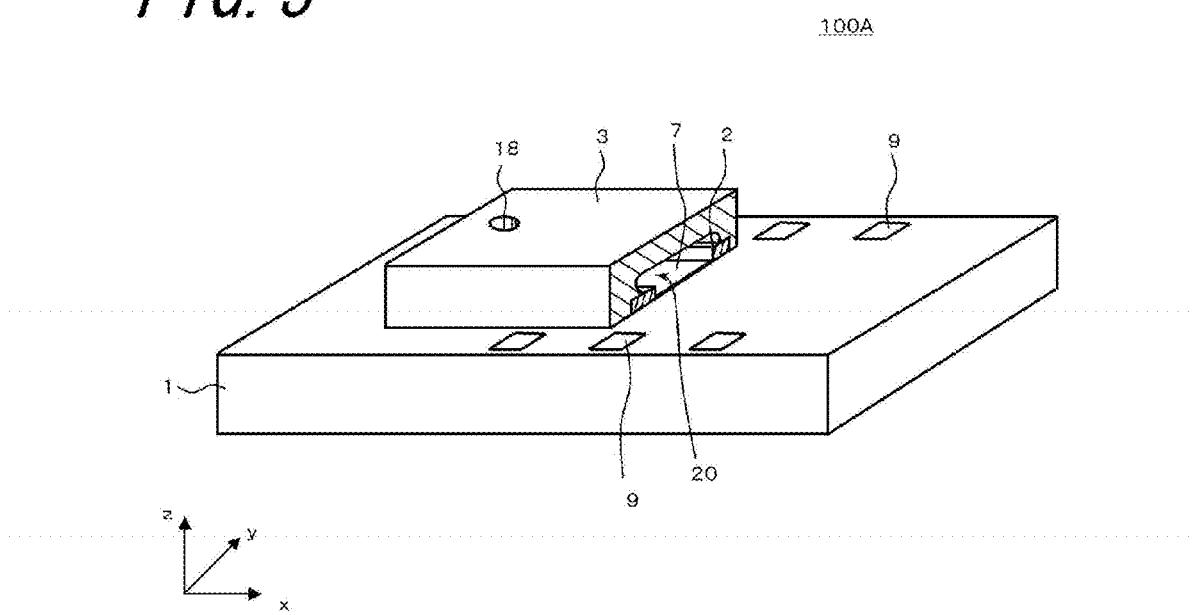
FIG. 3 is a partially cutaway perspective view of the analyte sensor shown in FIG. 1.

FIG. 3 shows a perspective view of the SAW sensor 100A, with one-half of the cover 3 removed. As shown in the drawing, a space 20 acting as a flow path for an analyte (solution) is formed inside the cover 3. The first through hole 18 is in communication with the space 20. That is, an analyte admitted from the first through hole 18 flows into the space 20.

The analyte solution which has flowed into the space 20 contains a target substance which is an analyte, and, the analyte reacts with a detecting portion made of a metal film 7 and so forth formed on the piezoelectric substrate.

The piezoelectric substrate 1 is formed of a piezoelectric single-crystal substrate, such for example as a lithium tantalate ($LiTaO_3$) single crystal, a lithium niobate ($LiNbO_3$) single crystal, or a quartz. The planar shape and dimensions of the piezoelectric substrate 1 may be determined arbitrarily. As an example, the piezoelectric substrate 1 has a thickness of 0.3 mm to 1 mm.

Figure 4:
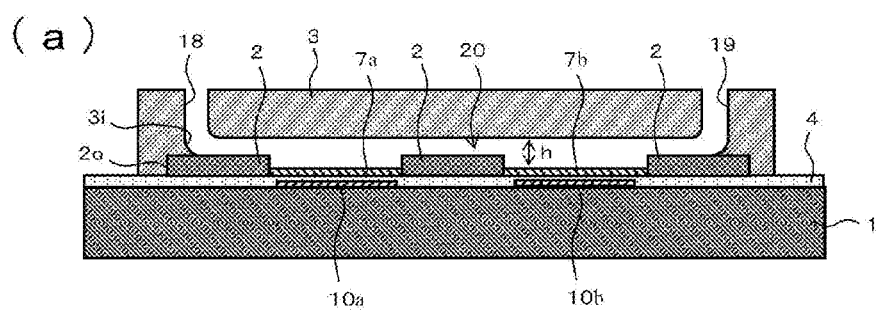
FIG. 4(a) is a sectional view taken along the line IVa-IVa shown in FIG. 2.
FIG. 4(b) is a sectional view taken along the line IVb-IVb shown in FIG. 2.
Figure 4:
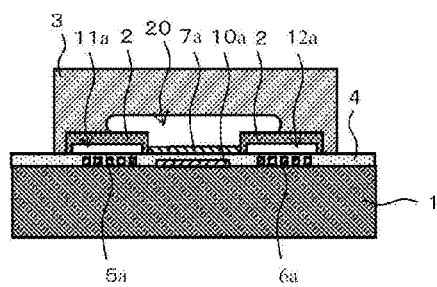

FIG. 4 shows a sectional view of the SAW sensor 100. FIG. 4(a) is a sectional view taken along the line IVa-IVa shown in FIG. 2, and FIG. 4(b) is a sectional view taken along the line IVb-IVb shown in FIG. 2. Moreover, FIG. 5 shows a top view of the SAW sensor 100, with the cover 3 removed.

Figure 5:
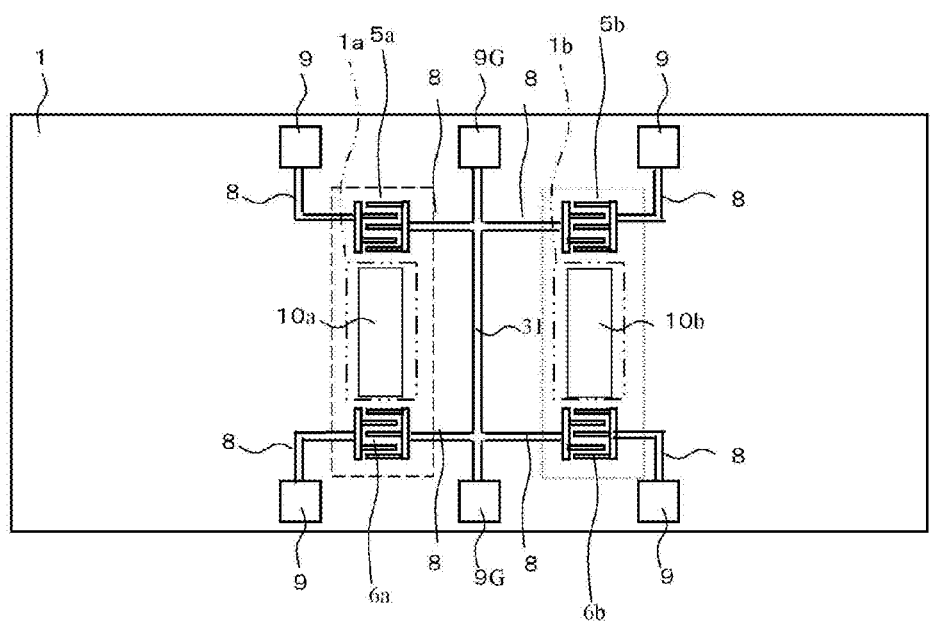
FIG. 5 is a top view of the analyte sensor shown in FIG. 1, with part thereof removed.

As shown in FIGS. 4(b) and 5, a first IDT electrode 5a, a second IDT electrode 6a, a reference first IDT electrode 5b, and a reference second IDT electrode 6b are formed on the upper surface of the piezoelectric substrate 1. The first IDT electrode 5a and the reference first IDT electrode 5b are intended for generation of predetermined SAW, and the second IDT electrode 6a and the reference second IDT electrode 6b are intended to receive SAW generated by the first IDT electrode 5a and SAW generated by the reference first IDT electrode 5b, respectively. In order for the second IDT electrode 6a to receive SAW generated by the first IDT electrode 5a, the second IDT electrode is placed on a propagation path of SAW generated by the first IDT electrode. The reference second electrode 6b is placed similarly in relation to the reference first IDT electrode 5b.

Since the reference first IDT electrode 5b and the reference second electrode 6b are similar to the first IDT electrode 5a and the second IDT electrode 6a, respectively, in what follows, the first IDT electrode 5a and the second IDT electrode 6a will be quoted by way of illustration.

The first IDT electrode 5a and the second IDT electrode 6a comprise a pair of comb-like electrodes (refer to FIG. 5). Each of the comb-like electrodes includes two bus bars opposed to each other and a plurality of electrode fingers extending from one of the bus bars toward the other. The comb-like electrode pair is placed so that the plurality of electrode fingers are arranged in an interdigitated pattern. The first IDT electrode 5a and the second IDT electrode 6a constitute a transversal-type IDT electrode.

Frequency characteristics can be designed on the basis of the number of the electrode fingers of the first IDT electrode 5a and the second IDT electrode 6a, the distance between the adjacent electrode fingers, the crossing width of the electrode fingers, etc. used as parameters. The types of SAW excited by the IDT electrode include: Rayleigh wave; Love wave; and Leaky wave, and, in the detection element 3, Love wave is utilized.

An elastic member for suppressing SAW reflection may be provided in a region outside of the first IDT electrode 5a in the propagation direction of SAW. The frequency of SAW can be set within a range of from several megahertz (MHz) to several gigahertz (GHz), for example. Particularly, it is advisable to set the SAW frequency within a range of from several hundred MHz to 2 GHz as a matter of practicality, and also, this makes it possible to achieve downsizing of the piezoelectric substrate 1 with a consequent miniaturization of the SAW sensor 100A.

The first IDT electrode 5a and the second IDT electrode 6a are each connected to a pad 9 via a wiring line 8. A signal is inputted from the outside to the first IDT electrode 5a through the pad 9 and the wiring line 8, and is outputted to the outside from the second IDT electrode 6a. As shown in FIG. 5, by separately providing a pad for the signal input side and a pad for the signal output side, on the opposite sides, respectively, of the piezoelectric substrate 1, it is possible to lessen the influence of a signal from the input side and a signal from the output side.

A short-circuit electrode 10a is formed in a first region 1a which is a region of the upper surface of the piezoelectric substrate 1 which is located between the first IDT electrode 5a and the second IDT electrode 6a. The short-circuit electrode 10a is intended to cause electrical short-circuiting in a part of the upper surface of the piezoelectric substrate 1 which serves as the SAW propagation path. The provision of the short-circuit electrode 10a makes it possible to, depending on the type of SAW, reduce SAW losses. It can be considered that the loss-reduction effect brought about by the short-circuit electrode 10a becomes especially high when Leaky wave is used as SAW.

For example, the short-circuit electrode 10a has a rectangular shape elongated along the SAW propagation path from the first IDT electrode 5a toward the second IDT electrode 6a. The width of the short-circuit electrode 10a in a direction perpendicular to the SAW propagation direction (x direction) is equal to, for example, the crossing width of the electrode fingers of the first IDT electrode 5a. Moreover, the first IDT electrode-sided end of the short-circuit electrode 10a in a direction parallel to the SAW propagation direction (y direction) is spaced away from the center of the electrode finger situated at the end of the first IDT electrode 5a by a distance equal to one-half wavelength of SAW. Likewise, the second IDT electrode-sided end of the short-circuit electrode 10a in the y direction is spaced away from the center of the electrode finger situated at the end of the second IDT electrode 6a by a distance equal to one-half wavelength of SAW.

The short-circuit electrode 10a may be in an electrically floating state, or alternatively, a pad 9 for ground potential may be provided, and the short-circuit electrode 10a may be connected to this pad 9 so as to stand at a ground potential. In the case where the short-circuit electrode 10a is set to the ground potential, it is possible to suppress propagation of a direct wave resulting from electromagnetic coupling between the first IDT electrode 5a and the second IDT electrode 6a.

Likewise, a short-circuit electrode 10b is formed in a first region 1b which is a region between two electrodes, namely the reference first IDT electrode 5b and the reference second IDT electrode 6b.

The first IDT electrode 5a, the second IDT electrode 6a, the reference first IDT electrode 5b, the reference second IDT electrode 6b, the short-circuit electrodes 10a and 10b, the wiring line 8, and the pad 9 are made of aluminum, an alloy of aluminum and copper, or the like, for example. Moreover, the electrodes may be given a multilayer structure. In the case of adopting the multilayer structure, for example, the first layer is made of titanium or chromium, and the second layer is made of aluminum or an aluminum alloy.

The first IDT electrode 5a, the second IDT electrode 6a, the reference first IDT electrode 5b, the reference second IDT electrode 6b, and the short-circuit electrodes 10a and 10b are covered with a protective film 4. The protective film 4 contributes to the protection of each of the electrodes and the wiring from oxidation, for example. The protective film 4 is made of silicon oxide, aluminum oxide, zinc oxide, titanium oxide, silicon nitride, silicon, or the like. In the SAW sensor 100A, silicon dioxide ($SiO_2$) is used for the protective film 4.

The protective film 4 is formed over the entire upper surface of the piezoelectric substrate 1, with the pads 9 exposed. The first IDT electrode 5a and the second IDT electrode 6a are covered with the protective film 4. This makes it possible to suppress the corrosion of the IDT electrodes.

The protective film 4 has a thickness of 100 nm to 10 μm, for example. The protective film 4 does not necessarily have to be formed over the entire upper surface of the piezoelectric substrate 1, and therefore, for example, it may be formed so as to cover only the central area of the upper surface of the piezoelectric substrate 1, with the other area along the outer periphery of the upper surface of the piezoelectric substrate 1 including the pads 9 exposed.

As shown in FIG. 4(*a*), the first IDT electrode 5*a* is accommodated in a first vibration space 11*a*, and the second IDT electrode 6*a* is accommodated in a second vibration space 12*a*. This makes it possible to separate the first IDT electrode 5*a* and the second IDT electrode 6*a* from outside air and an analyte solution, and thereby protect the first IDT electrode 5*a* and the second IDT electrode 6*a* against a corrosion-inducing substance such as water. Moreover, by securing the first vibration space 11*a* and the second vibration space 12*a*, the first IDT electrode 5*a* and the second IDT electrode 6*a* can be kept in a condition where SAW excitation will not be seriously hindered.

The first vibration space 11*a* and the second vibration space 12*a* can be formed by joining a plate-like body 2 having recesses for creating these vibration spaces to the piezoelectric substrate 1.

Likewise, a first vibration space 11*b* and a second vibration space 12*b* are secured for the reference first IDT electrode 5*b* and the reference second IDT electrode 6*b*.

Although the first vibration space 11 and the second vibration space 12 of the SAW sensor 100A are each a rectangular parallelepiped space, the shape of the vibration space is not limited to the rectangular parallelepiped shape, and can therefore be changed to another shape on an as needed basis with consideration given to the form or arrangement of the IDT electrodes, and more specifically, for example, the vibration space may be dome-shaped as seen in a sectional view, or may be elliptically shaped as seen in a plan view.

The plate-like body 2 has, in a region between the recesses for creating the first vibration space 11*a* and the second vibration space 12*a*, a through part formed therethrough in a thickness direction thereof. This through part is intended for the formation of a metal film 7*a* on the SAW propagation path. That is, when the plate-like body 2 joined to the piezoelectric substrate 1 is seen in a plan view, at least part of the propagation path of SAW propagating from the first IDT electrode 5*a* to the second IDT electrode 6*a* is exposed from the through part, and the metal film 7*a* is formed on this exposed part.

Likewise, the plate-like body 2 also has, in a region between the recesses for creating the first vibration space 11*b* and the second vibration space 12*b*, another through part formed therethrough in the thickness direction thereof. This through part is intended for the formation of a metal film 7*b* on the SAW propagation path.

The plate-like body 2 having such a shape can be formed with use of a photosensitive resist, for example.

The metal film 7*a* exposed from the through part of the plate-like body 2 constitutes an analyte detecting portion for an analyte solution. The metal film 7*a* has a double-layer structure consisting of titanium or chromium and gold laminated thereon, for example. An aptamer such for example as a nucleic acid- or peptide-made aptamer is immobilized on the surface of the metal film 7*a*. Upon occurrence of contact between an analyte solution and the aptamer-immobilized metal film 7*a*, a specific target substance contained in the analyte solution is bound to the aptamer adaptable to the target substance. In such a structure, the analyte is bound to the aptamer, and, as adsorption proceeds, the mass of the metal film 7*a* is monotonically increased. That is, there arises a monotonic increase in mass in response to analyte detection. Note that the mass of the metal film 7*a* is monotonically increased only during the interval when the analyte is being continuously supplied onto the metal film 7*a*. For example, in a case where a buffer solution is supplied subsequent to the supply of the analyte before and after the supply of the analyte solution, even if the analyte passes over the metal film 7*a* and the mass is reduced by the separation between the analyte and the aptamer, there is no problem.

Moreover, the metal film 7*b* exposed from the other through part of the plate-like body 2 constitutes a reference measuring portion. The metal film 7*b* has a double-layer structure consisting of titanium or chromium and gold laminated thereon, for example. The surface of the metal film 7*b* is free from aptamer immobilization so as not to exhibit reactivity to the analyte. Instead, the metal film may be subjected to surface treatment to cause reduced response to the analyte solution for stabilizing purposes.

In order to assess the properties and so forth of the analyte solution through the use of SAW, to begin with, a predetermined voltage (signal) is applied, through the pad 9 and the wiring line 8, to the first IDT electrode 5*a* from external measurement equipment. Then, the surface of the piezoelectric substrate 1 is excited within the region where the first IDT electrode 5*a* is formed, thereby producing SAW having a predetermined frequency. Part of the thusly produced SAW passes through the first region 1*a* which is the region between the first IDT electrode 5*a* and the second IDT electrode, and then reaches the second IDT electrode 6*a*. At this time, in the metal film 7*a* situated on the first region 1*a*, the aptamer immobilized on the metal film 7*a* is bound to the specific target substance contained in the analyte solution, and the weight of the metal film 7 changes by a weight corresponding to the bound amount, which results in variations in the phase characteristics and so forth of SAW passing under the metal film 7*a*. Upon the SAW which has undergone characteristics variations reaching the second IDT electrode 6*a*, a corresponding voltage is developed in the second IDT electrode 6*a*. This voltage is outputted, through the wiring line 8 and the pad 9, to the outside as a detection signal in the form of an AC signal. The properties and ingredients of the analyte solution can be examined by processing the signal in the mixer 130 as shown in FIG. 1.

That is, the piezoelectric substrate 1, the metal film 7*a* acting as the analyte detecting portion formed on the piezoelectric substrate 1, the first IDT electrode 5*a*, and the second IDT electrode 6*a* constitute a detection element 110A.

Likewise, in the same space 20, the other metal film 7*b* free from aptamer immobilization is disposed, and, an AC signal outputted from the reference second IDT electrode 6*b* in the wake of inputting of a signal from the reference first IDT electrode 5*b* is defined as a reference signal for use in calibration of signal fluctuations caused by environmental variations such as variations in temperature characteristics and humidity.

That is, the piezoelectric substrate 1, the metal film 7*b* acting as the reference measuring portion formed on the piezoelectric substrate 1, the reference first IDT electrode 5*b*, and the reference second IDT electrode 6*b* constitute a reference element 120A.

In the case of conducting measurement through the use of SAW in that way, as has already been described, there is a need to provide a protective film such as silicon oxide to protect the IDT electrodes and so forth, but, as the result of a survey by the inventors of the present application, it has been found that, if such a protective film is exposed inside the flow path for an analyte solution, a trouble such as great variations of the detection sensitivity or deterioration of the detection sensitivity is easy to occur.

Although the cause of such a trouble has not been clarified, this is probably attributable to a phenomenon in which an aptamer adheres to the protective film 4 exposed from the through part when the aptamer is immobilized on the metal film 7a and consequently a desired amount of the aptamer cannot be immobilized on the metal film 7a, or a target substance (analyte) adheres to the protective film 4 when an analyte solution is charged into the space 20.

In light of this, the SAW sensor 100A is designed so that the protective film 4 is not exposed inside the space 20 acting as a flow path.

In the interest of uniformity in the amount of an analyte solution during measurement, in the SAW sensor 100A is provided the space 20 acting as a flow path for an analyte solution. The space 20 of the SAW sensor 100A is a space surrounded with the inner surface of the cover 3, the outer surface of the plate-like body 2, and the upper surface of the metal film 7a, 7b.

Since such a space 20 has basically a constant volumetric capacity, by charging an analyte solution into the space 20, it is possible to render the amount of the analyte solution uniform during measurement.

In charging an analyte into the space 20, a capillary phenomenon is exploited in the SAW sensor 100A. Specifically, by adjusting each of the size (diameter, for example) of the first through hole 18 acting as an analyte inlet and the size (width and height, for example) of the space 20 acting as the flow path for an analyte solution to a predetermined value in consideration of the type of the analyte solution, the material used for the cover 3, etc., it is possible to urge an analyte to move from the inlet to the flow path and eventually to the analyte detecting portion by exploiting the capillary phenomenon. The width w (FIG. 4(*a*)) of the space 20 falls in a range of from 0.5 mm to 3 mm, for example, and, the height h (FIG. 4(*a*)) thereof falls in a range of from 0.05 mm to 0.5 mm, for example. The diameter of the first through hole 18 falls in a range of from 50 µm to 500 µm, for example.

With the formation of the first through hole 18 and the space 20, simply by bringing an analyte into contact with the opening of the first through hole 18, the analyte can automatically be drawn into the space 20 by capillary action, and the space 20 is filled with the analyte. Thus, according to the SAW sensor 100, the SAW sensor in itself includes an analyte-solution suction mechanism, wherefore the suction of an analyte can be effected without the necessity of using an instrument such as a pipette. Note that the shape of the first through hole 18 acting as the analyte inlet is not limited to a cylindrical shape, and therefore, for example, the first through hole 18 may be so shaped that its diameter becomes smaller or larger gradually toward the space 20, or may have a rectangular opening. Moreover, the forming position of the first through hole 18 is not limited to the ceiling part of the cover 3, but may be in a side wall of the cover 3.

In addition to the first through hole 18, the second through hole 19 is formed in the cover 3. The second through hole 19 is located at an end part of the cover opposite to the end part bearing the first through hole 18, and is in communication with the space 20. By virtue of such a second through hole 19, when an analyte enters the space 20, air which is originally present in the space 20 is expelled to the outside from the second through hole 19, whereby the analyte can be easily admitted into the space 20.

The corners of that part of the space 20 which is defined by the inner surface of the cover 3 are rounded off. For example, as shown in the sectional view of FIG. 4, the juncture of the first through hole 18 and the space 20, the juncture of the second through hole 19 and the space 20, and the juncture of the inner periphery of the cover 3 and the plate-like body 2 are each rounded off.

If the corners of the space 20 acting as the flow path for an analyte solution become angular, an analyte solution will accumulate at the corner, and consequently the analyte tends to be stagnant. In the presence of analyte stagnation, for example, there arise concentration variations within the target substance of the analyte charged in the space 20, which gives rise to a problem such as detection sensitivity deterioration. By contrast, where the space 20 has rounded corners as in the analyte sensor 100A, the analyte is less prone to stagnation, whereby the concentration of the target substance can be rendered uniform throughout the space 20.

Moreover, it is advisable to form the first through hole 18 acting as the analyte inlet in a position as close to the end of the space 20 as possible from the viewpoint of preventing analyte accumulation.

For example, the cover 3 is made of polydimethylsiloxane. With use of polydimethylsiloxane as the material for the cover 3, the cover 3 can be given a desired shape, for example, the cover 3 can be configured to have rounded corners. Moreover, with use of polydimethylsiloxane, the ceiling part and the side wall of the cover 3 can be made thick relatively easily. For example, the ceiling part and the side wall of the cover 3 have a thickness of 1 mm to 5 mm.

In the analyte sensor 100A, the cover 3 is disposed, with the outer periphery of its lower surface kept in contact with the protective film 4 situated around the plate-like body 2, so as to be joined to the protective film 4 at the contacted part. In other words, the cover 3 can be deemed to be joined to the piezoelectric substrate 1 through the protective film 4. In a case where the cover 3 is made of polydimethylsiloxane, and the protective film 4 is made of $SiO_2$, by performing oxygen plasma treatment on the surface of the cover 3 to be contacted by the protective film 4, it is possible to join the cover 3 directly to the protective film 4 without the necessity of using an adhesive or the like. Although the reason why the cover 3 and the protective film 4 can be directly joined to each other under such a condition has not been clarified, this is probably because a covalent bond of Si and O is formed between the cover 3 and the protective film 4.

As has already been described, the substrate is shared between the detection element 110A and the reference element 120A. In such a structure, there is the possibility of occurrence of crosstalk between signals on both elements. Therefore, as shown in FIG. 5, a reference potential line 31 connected to a reference potential is disposed between a region serving as the detection element 110A indicated by broken lines in the drawing and a region serving as the reference element 120A indicated by dotted lines in the drawing on the piezoelectric substrate 1. By virtue of the reference potential line 31, occurrence of crosstalk between the detection element 110A and the reference element 120A can be prevented, wherefore a high-sensitivity analyte sensor 100A can be provided.

As shown in FIG. 5, the reference potential line 31 is connected with one of the paired comb-like electrodes constituting each of the first IDT electrode 5a, the second IDT electrode 6a, the reference first IDT electrode 5b, and the reference second IDT electrode 6b. Out of the paired comb-like electrodes constituting each of the first IDT electrode 5a, the second IDT electrode 6a, the reference first IDT electrode 5b, and the reference second IDT electrode 6b, the electrode to be connected to the reference potential is located at the side on which the reference potential line 31 is disposed. In other words, of the paired comb-like electrodes, the inwardly located electrode is connected to the reference potential.

Such an arrangement makes it possible to facilitate the layout of the wiring lines 8 for the detection element 110A and the reference element 120A, as well as to render the wiring lines 8 uniform in length. Thus, the reference signal from the reference element 120A becomes a more accurate signal for reference purposes.

Moreover, in a case where the structure including the detection element 110A and the reference element 120A and the structure including the measurement portion 140 and the detection amount calculation portion 150 are provided independently of each other, in the structure including the measurement portion 140 and the detection amount calculation portion 150, it is desirable to conduct wiring installation in conformity with the arrangement of the wiring lines 8 on the piezoelectric substrate 1. This configuration makes it possible to prevent crosstalk even in the structure including the measurement portion 140 and the detection amount calculation portion 150.

Modified Example

Arrangement of Analyte Flow Path, Detection Element, and Reference Element

Figure 6:
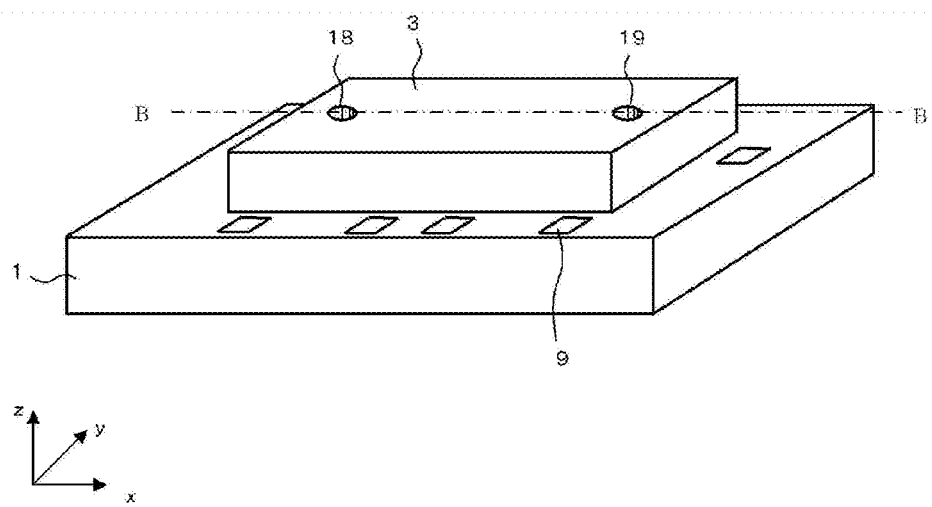
FIG. 6 shows a modified example of the analyte sensor shown in FIG. 1.
Figure 6:
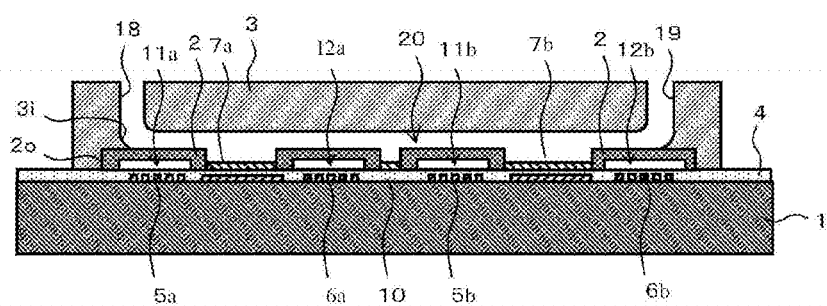

Although in the above embodiment it is described that the constituent components are so arranged that the direction of elongation of the space 20 acting as the analyte flow path and the propagation direction of surface acoustic waves in the detection element 110A and the reference element 120A are perpendicular to each other, as in an analyte sensor 100B as shown in FIG. 6, the directions may be parallel to each other.

Modified Example

Arrangement of Analyte Flow Path, Detection Element, and Reference Element

Figure 7:
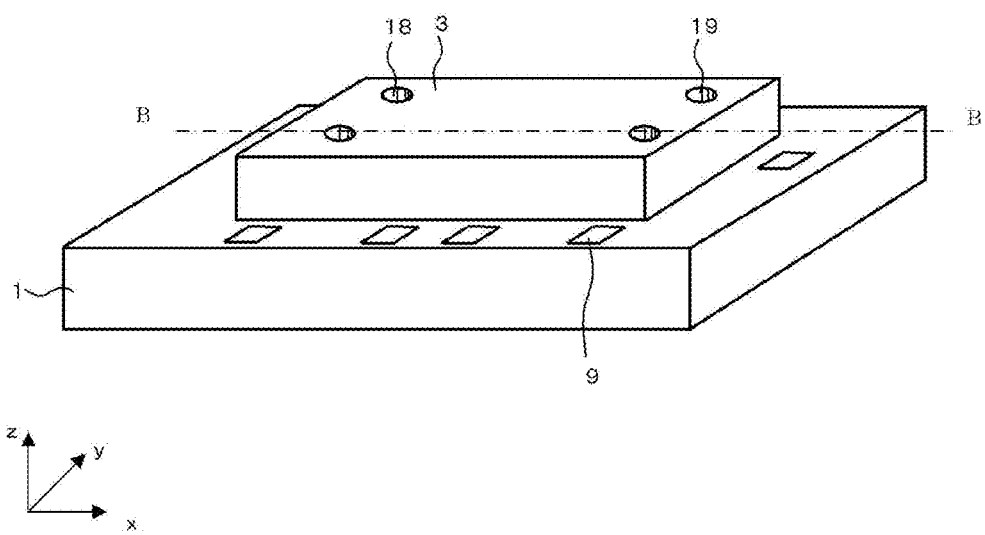
FIG. 7 shows a modified example of the analyte sensor shown in FIG. 1.
Figure 7:
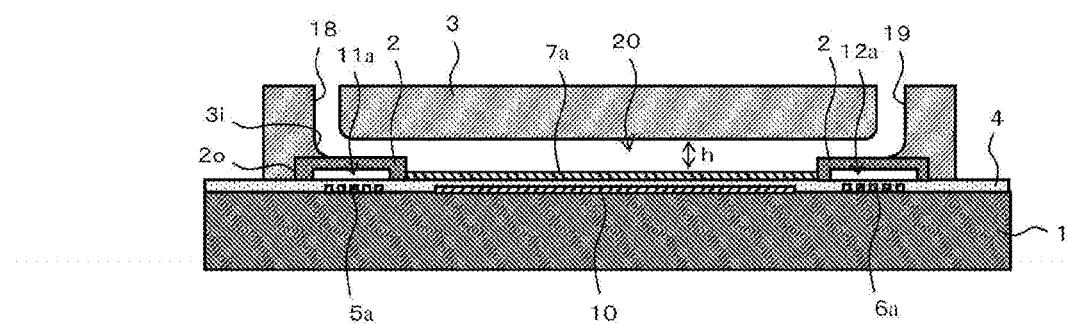

Although in the above embodiment it is described that the space 20 acting as the analyte flow path is shared between the detection element 110A and the reference element 120A, as in an analyte sensor 100C as shown in FIG. 7, the space 20 may be provided specifically for each of the detection element 110A and the reference element 120A. While, in the example shown in FIG. 7, the inlet 18 is provided for each space 20 on an individual basis, the inlet can be shared between two analyte flow paths. Moreover, while, in the example shown in FIG. 7, like the example shown in FIG. 6, the SAW propagation direction and the analyte-flow-path elongation direction coincide with each other, the SAW propagation direction and the analyte-flow-path elongation direction may be perpendicular to each other.

Modified Example

Piezoelectric Substrate 1

Although in the above embodiment it is described that a piezoelectric substrate is shared between the detection element 110A and the reference element 120A, an element substrate for the detection element 110A and a reference element substrate for the reference element 120A may be provided independently of each other. In this case, occurrence of crosstalk between the detection element 110A and the reference element 120A can be prevented without fail. Moreover, in this case, it is advisable to provide two separate base bodies that hold the element substrate and the reference element substrate, respectively.

Modified Example

π/2 Delay Line

Figure 8:
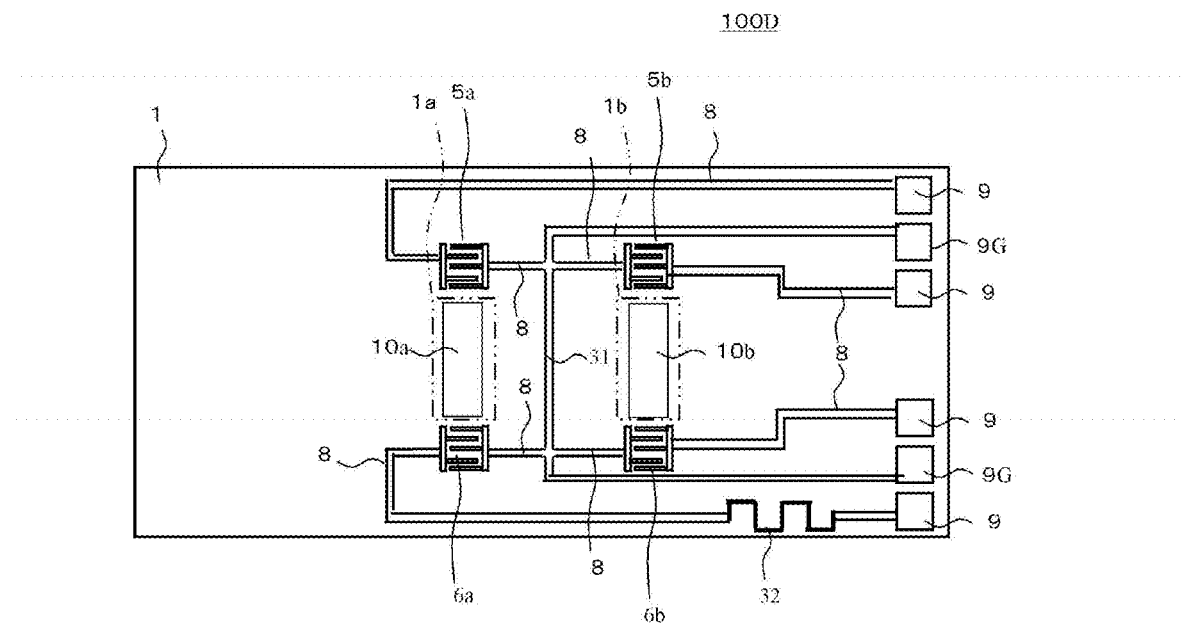
FIG. 8 shows a modified example of the analyte sensor shown in FIG. 1.

Although in the above embodiment it is described that the first IDT electrode 5a, the second IDT electrode 6a, the reference first IDT electrode 5b, and the reference second IDT electrode 6b are connected to their nearby pads 9 without taking any detour, as in an analyte sensor 100D as shown in FIG. 8, a π/2 delay line 32 may be disposed between the pad and, one of the paired comb-like electrodes constituting the second IDT electrode 6a, the one comb-like electrode being not connected to the reference potential. In the analyte sensor 100A, since signal processing operation is performed by the heterodyne system, it follows that a signal makes a sine curve. Therefore, the slope of the sine curve with respect to phases corresponding to 0° and ±180° decreases, which results in a decline in sensitivity. However, in the analyte sensor, the vicinity of 0° generally corresponds to a rise of a signal change entailed by analyte detection, wherefore it is desired that this range should be measured with high sensitivity. In light of this, by providing the π/2 delay line 32 for one of the constituent electrodes of the second IDT electrode 6a to be connected to the mixer, it is possible to change the signal phase and thereby achieve enhancement in sensitivity in the vicinity of 0°.

Such a π/2 delay line 32 can be prepared by forming a conductor film on the piezoelectric substrate 1, and then performing patterning thereon so as to obtain a necessary line length.

Moreover, as shown in FIG. 8, by arranging the pads 9 side by side at the edge of one side constituting the piezoelectric substrate 1, the handling becomes easier, and also the wiring lines 8 can be laid out with consistency, wherefore wiring-induced signal delay, signal shift, and noise superimposition can be suppressed.

Another Embodiment

Figure 9:
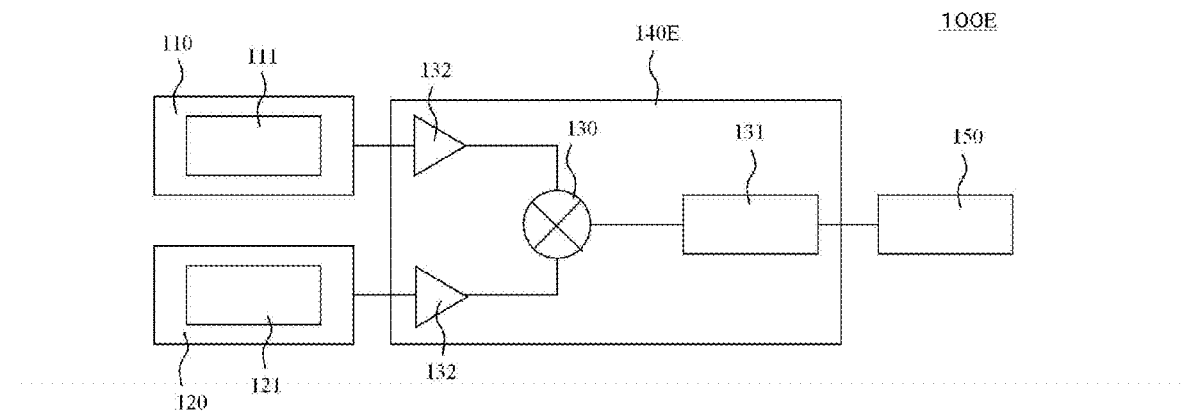
FIG. 9 is a principled configuration diagram showing the analyte sensor in accordance with another embodiment of the invention.

In the above embodiment it is described that signals from the detection element 110 and the reference element 120 are synthesized directly by the mixer 130. By contrast, in an analyte sensor 100E as shown in FIG. 9, low-noise amplifiers 132 are disposed between the detection element 110 and the mixer 130, and between the reference element 120 and the mixer 130, respectively. That is, a measurement portion 140E includes the low-noise amplifiers 132, the mixer 130, and the low-pass filter 131.

In the SAW sensor, in general, high sensitivity can lead to significant variations in amplitude characteristics. That is, when the SAW sensor is designed to have high sensitivity by making adjustment to the thickness of the protective film 4 and so forth, a large loss may occur, which causes the possibility of a failure of accurate measurement. On the other hand, when a signal inputted to the mixer 130 is small, noise may be increased, which causes the possibility of impairment of detection accuracy.

Furthermore, when signals inputted to the detection element 110 and the reference element 120 are large, there is the possibility of crosstalk between output signals on the detection element 110 and the reference element 120. In addition, when signals inputted to the detection element 110 and the reference element 120 are large, there is the possibility that output signals from the detection element 110 and the reference element 120 will leak to the outside as electromagnetic waves.

It will thus be seen that the placement of the low-noise amplifiers 132 between the detection element 110 and the mixer 130 and between the reference element 120 and the mixer 130, is important for the attainment of high detection accuracy.

EXAMPLES

One and the same analyte was measured by each of the analyte sensor 100E and the analyte sensor 100 devoid of the low-noise amplifiers 132. Specifically, the measurement was conducted under conditions where: the center frequency of SAW is 414 MHz; the IDT electrodes 5 and 6 are made of Al and are 300 nm in thickness; the protective film 4 is made of $SiO_2$ and is 100 nm in thickness; and the distance between the first IDT electrode 5a and the IDT electrode 6a is 300λ (λ represents the wavelength of SAW propagating through the metal film 7 after being excited by the first IDT electrode 5a). Moreover, there were prepared analytes that have contained target concentrations of 100 nM, 200 nM, and 500 nM, respectively, and these analytes were supplied to the analyte sensors. The measurement was also conducted by means of a vector network analyzer (VNA) as a reference example.

Figure 11:
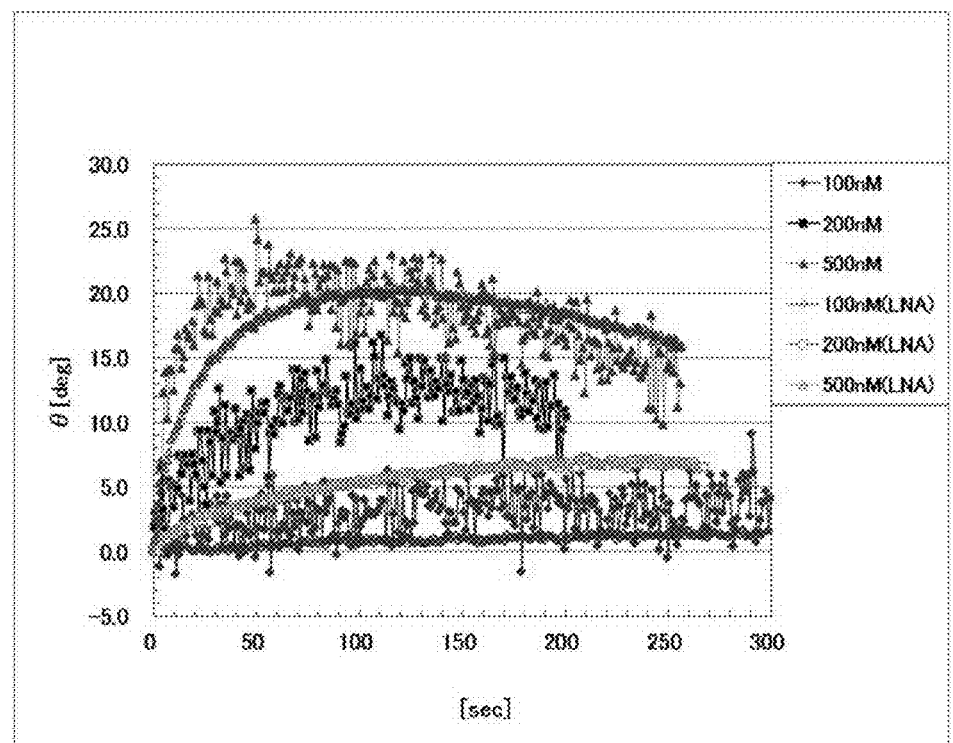
FIG. 11 is a chart showing a correlation between measurement time and phase difference in the example of the invention.

FIG. 11 shows the result of actual measurement of the values of changes in phase with respect to time since the supply of analyte solutions to the analyte sensors 100 and 100E. In FIG. 11, the amount of phase change (θ) is taken along the ordinate axis, and time (sec) is taken along the abscissa axis. The solid explanatory legends indicate the result of measurement by the LNA-free analyte sensor 100, whereas the hollow explanatory legends indicate the result of measurement by the LNA-equipped analyte sensor 100E. As shown in FIG. 11, it can be confirmed that measurement has been conducted properly for a long period of time. That is, the analyte sensor pursuant to the invention can be confirmed to be capable of measurement in an even wider phase range by the heterodyne system. Also, the dependence of the analyte solution on concentration can be confirmed.

Figure 12:
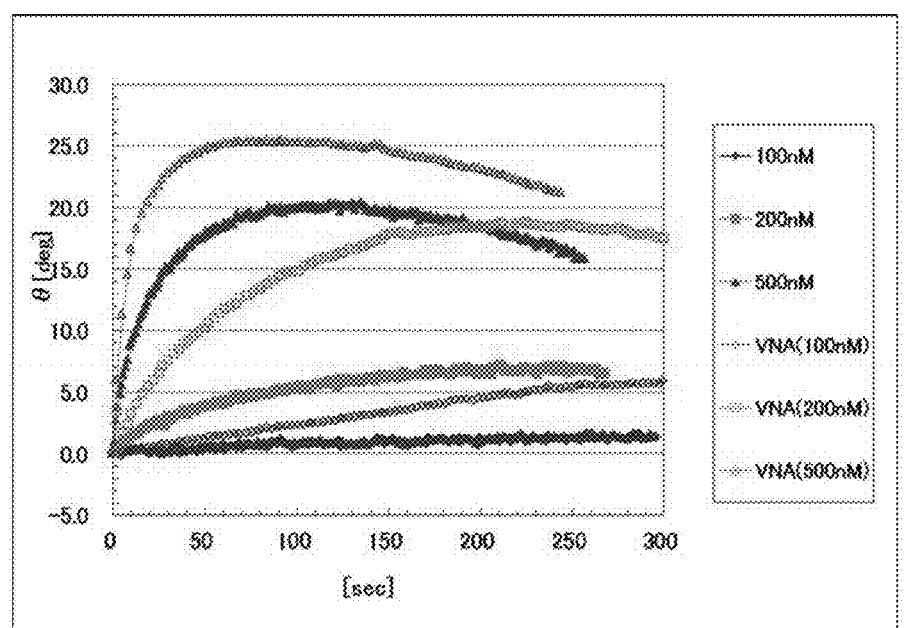
FIG. 12 is a chart for comparison between the example of the invention and VNA.

Moreover, the analyte sensor 100E equipped with the low-noise amplifiers 132 was found to be far smaller than the analyte sensor devoid of the low-noise amplifiers 132 in respect of variations in phase change value. Specifically, as shown in FIG. 12, the analyte sensor 100E compares favorably in measurement accuracy with VNA which is capable of low-level measurement and is also able to increase the magnitude of an input signal in itself. Note that FIG. 12 is a chart showing the result of measurement by VNA and the result of measurement by the analyte sensor 100E.

(Method for Measuring Detection Amount of Analyte)

An analyte sensing method adopted in the analyte sensor will be described.

(Analyte-Solution Supplying Step)

The first step is an analyte-solution supplying step of supplying an analyte containing a target to the analyte detecting portion of the detection element that is increased in mass in response to target adsorption or reaction with the target, and the reference detecting portion of the reference element that undergoes neither target adsorption nor reaction with the target.

(Determination Step)

Next, in accordance with the heterodyne system, a measurement signal is obtained from a detection signal which is an AC signal responsive to mass variations in the analyte detecting portion and a reference signal from the reference detecting portion that is an AC signal relative to the detection signal.

Then, as a phase-change value determination step, two candidate phase-change values of a positive value and a negative value, are derived from the measurement signal, and whether the phase is positive or negative is judged on the basis of temporal changes in measurement signal strength, so that a phase change value can be determined from the two candidate phase-change values. In this example, since the measurement signal is processed by the heterodyne system, it follows that there are two candidate phase-change values, wherefore phase changes cannot be directly ascertained from signal strength. Note that the analyte detecting portion is so designed that the mass is increased in response to target detection, wherefore there is a monotonic increase in phase change. In this regard, by adding a step of examining temporal changes in measurement signal strength, it is possible to identify whether the strength is on the increase or on the decrease, and thereby make a decision about which one of the two candidate phase-change values to be selected. Specifically, when the measurement signal strength is decreased with time, the positive value is determined as the phase change value, and when the measurement signal strength is increased with time, the negative value is determined as the phase change value.

In order to accomplish such steps, specifically, it is advisable to conduct measurement of mixed signal strength at least twice at time-spaced intervals. It is also advisable to carry out measurement signal sampling consecutively.

(Calculation Step)

Lastly, a calculation step of calculating the detection amount of an analyte on the basis of the thusly determined phase change value, is performed.

By following the above-described procedure, the detection amount of an analyte can be measured.

Moreover, in the determination step, each of the detection signal and the reference signal may be amplified, and, in this case, a measurement signal is obtained on the basis of these detection and reference signals amplified by the heterodyne system.

The invention is not limited to the embodiments as described hereinabove, and may therefore be carried out in various forms. For example, although the analyte sensor 100A is illustrated as being designed so that the detecting portion comprises the metal film 7 and the aptamer immobilized on the surface of the metal film 7, in a case where the target substance contained in the analyte solution reacts with the metal film 7, the detecting portion may be composed solely of the metal film 7 without using an aptamer.

Although in the above embodiment it is described that the analyte detecting portion is monotonically increased in mass in response to adsorption of a target contained in an analyte or reaction with the target, it is possible to employ an analyte detecting portion which is monotonically decreased in mass in response to reaction with a target contained in an analyte. In this case, for example, the analyte detecting portion can be implemented by immobilizing, on a Au film, a reactive group which exhibits reactivity to the target and has a conformation in which part of the reactive group comes off through the reaction with the target. Then, a choice between the condition (2) and the condition (4) is made for phase-change value calculation based on the heterodyne system. For example, under the condition (4), when the measurement signal strength is increased with time, the positive candidate phase-change value is assigned, and when the measurement signal strength is decreased with time, the negative candidate phase-change value is assigned. Such a configuration affords adaptability to an analyte detecting portion of a type which is monotonically changed in mass in response to adsorption of a target contained in an analyte or reaction with the target.

REFERENCE SIGNS LIST

1: Piezoelectric substrate
2: Plate-like body
3: Cover
4: Protective film
5a: First IDT electrode
5b: Reference first IDT electrode
6a: Second IDT electrode
6b: Reference second IDT electrode
7a, 7b: Metal film
8: Wiring line
9: Pad
10: Short-circuit electrode
11a, 11b: First vibration space
12a, 12b: Second vibration space
20: Space
31: Reference potential line
32: $\pi/2$ delay line

The invention claimed is:

1. An analyte sensor, comprising:
a detection element comprising an analyte detecting portion which is monotonically changed in mass in response to adsorption of a target provided in an analyte or reaction with the target, the detection element configured to output a detection signal of AC responsive to mass variations in the analyte detecting portion;
a reference element comprising a reference measuring portion which undergoes neither adsorption of the target nor reaction with the target, the reference element configured to output a reference signal of AC relative to the detection signal;
a measurement portion which determines two candidate phase-change values of a positive candidate phase-change value and a negative candidate phase-change value, from a measurement signal which is obtained from the detection signal and the reference signal in accordance with a heterodyne system,
the measurement portion configured to output the positive candidate phase-change value as a phase change value when measurement signal strength is decreased with time, and configured to output the negative candidate phase-change value as a phase change value when measurement signal strength is increased with time, in a case where a mass of the analyte detecting portion is monotonically increased and the detection signal is obtained by subtracting the detection signal from the reference signal in accordance with the heterodyne system, or where the mass of the analyte detecting portion is monotonically decreased and the detection signal is obtained by subtracting the reference signal from the detection signal in accordance with the heterodyne system, and
the measurement portion configured to output the negative candidate phase-change value as a phase change value when measurement signal strength is decreased with time, and configured to output the positive candidate phase-change value as a phase change value when measurement signal strength is increased with time, in a case where the mass of the analyte detecting portion is monotonically increased and the detection signal is obtained by subtracting the reference signal from the detection signal in accordance with the heterodyne system, or where the mass of the analyte detecting portion is monotonically decreased and the detection signal is obtained by subtracting the detection signal from the reference signal in accordance with the heterodyne system; and
a detection amount calculation portion which calculates a detection amount of the analyte on a basis of the phase change value.

2. The analyte sensor according to claim 1, further comprising:
an analyte flow path through which an analyte solution containing the analyte is supplied to the analyte detecting portion and the reference measuring portion in order or simultaneously.

3. The analyte sensor according to claim 1, wherein the detection element comprises
a piezoelectric detection element substrate,
the analyte detecting portion, the analyte detecting portion being placed on the piezoelectric detection element substrate,
a detection first IDT electrode placed on the piezoelectric detection element substrate, the detection first IDT electrode configured to produce an elastic wave toward the analyte detecting portion, and
a detection second IDT electrode placed on the piezoelectric detection element substrate, the detection second IDT electrode configured to receive the elastic wave which has passed through the analyte detecting portion,
the reference element comprises
a piezoelectric reference element substrate,
the reference measuring portion, the reference measuring portion being placed on the reference element substrate,
a reference first IDT electrode placed on the reference element substrate, the reference first IDT electrode configured to produce an elastic wave toward the reference measuring portion, and
a reference second IDT electrode placed on the reference element substrate, the reference second IDT electrode configured to receive the elastic wave which has passed through the reference measuring portion,
the detection signal is an AC signal obtained when the elastic wave which has passed through the analyte detecting portion is received by the detection second IDT electrode, and
the reference signal is an AC signal obtained when the elastic wave which has passed through the reference measuring portion is received by the reference second IDT electrode.

4. The analyte sensor according to claim 3, further comprising:
a $\pi/2$ delay line configured to permit passage of the detection signal or the reference signal which are prior to acquisition of the measurement signal by the heterodyne system.

5. The analyte sensor according to claim 3,
wherein the detection element substrate and the reference element substrate are formed integrally with each other, and
further comprising a reference potential line located between a detection element region where the analyte detecting portion, the detection first IDT electrode, and the detection second IDT electrode are disposed, and a reference element region where the reference measuring portion, the reference first IDT electrode, and the reference second IDT electrode are disposed.

6. The analyte sensor according to claim 5, wherein the detection first IDT electrode, the detection second IDT electrode, the reference first IDT electrode, and the reference second IDT electrode are each composed of a pair of comb-like electrodes, and one of the pair of comb-like electrodes is connected to the reference potential line, respectively.

7. The analyte sensor according to claim 1, further comprising:

low-noise amplifiers which are disposed between the detection element and the measurement portion, and between the reference element and the measurement portion, respectively, the low-noise amplifiers being configured to amplify the detection signal from the detection element and the reference signal from the reference element, respectively.

8. An analyte sensing method, comprising:

an analyte solution supplying step of supplying an analyte solution containing an analyte in which a target is provided, to an analyte detecting portion of a detection element that is monotonically changed in mass in response to adsorption of the target or reaction with the target, and a reference detecting portion of a reference element that undergoes neither adsorption of the target nor reaction with the target;

a determination step of determining two candidate phase-change values of a positive candidate phase-change value and a negative candidate phase-change value, from a measurement signal which is obtained from a detection signal of AC responsive to mass variations in the analyte detecting portion and a reference signal of AC from the reference detecting portion, relative to the detection signal, in accordance with a heterodyne system, the positive candidate phase-change value being determined as a phase change value when measurement signal strength is decreased with time, and the negative candidate phase-change value being determined as a phase change value when measurement signal strength is increased with time, in a case where a mass of the analyte detecting portion is monotonically increased and the detection signal is obtained by subtracting the detection signal from the reference signal in accordance with the heterodyne system, or where the mass of the analyte detecting portion is monotonically decreased and the detection signal is obtained by subtracting the reference signal from the detection signal in accordance with the heterodyne system, and the negative candidate phase-change value being determined as a phase change value when measurement signal strength is decreased with time, and the positive candidate phase-change value being determined as a phase change value when measurement signal strength is increased with time, in a case where the mass of the analyte detecting portion is monotonically increased and the detection signal is obtained by subtracting the reference signal from the detection signal in accordance with the heterodyne system, or where the mass of the analyte detecting portion is monotonically decreased and the detection signal is obtained by subtracting the detection signal from the reference signal in accordance with the heterodyne system; and a calculation step of calculating an amount of the analyte detected on a basis of the phase change value.

9. The analyte sensing method according to claim 8, wherein, in the determination step, each of the detection signal and the reference signal is amplified, and a measurement signal is obtained on a basis of the detection signal amplified and reference signal amplified by the heterodyne system.

* * * * *